US006153225A

United States Patent [19]
Lee et al.

[11] Patent Number: 6,153,225
[45] Date of Patent: Nov. 28, 2000

[54] INJECTABLE FORMULATIONS OF NANOPARTICULATE NAPROXEN

[75] Inventors: Robert Lee, Gilbertsville, Pa.; Lan De Castro, Montclair, N.J.

[73] Assignee: Elan Pharma International Limited, Shannon, Ireland

[21] Appl. No.: 09/154,422

[22] Filed: Aug. 13, 1998

[51] Int. Cl.[7] .............................. A61K 9/50; B01J 13/02; B32B 5/16
[52] U.S. Cl. ......................... 424/501; 264/4.1; 264/4.33; 264/4.7; 428/402.21
[58] Field of Search .............................. 424/501; 264/4.1, 264/4.33, 4.7; 428/402.21

[56] References Cited

U.S. PATENT DOCUMENTS

| | | |
|---|---|---|
| 3,904,682 | 9/1975 | Fried et al. . |
| 4,009,197 | 2/1977 | Fried et al. . |
| 4,780,320 | 10/1988 | Baker . |
| 4,888,178 | 12/1989 | Rotini et al. . |
| 4,919,939 | 4/1990 | Baker . |
| 4,940,588 | 7/1990 | Sparks et al. . |
| 5,145,684 | 9/1992 | Liversidge et al. . |
| 5,200,193 | 4/1993 | Radebaugh et al. . |
| 5,354,556 | 10/1994 | Sparks et al. . |
| 5,462,747 | 10/1995 | Radebaugh et al. . |
| 5,480,650 | 1/1996 | Marchi et al. . |
| 5,510,118 | 4/1996 | Bosch et al. . |
| 5,770,222 | 6/1998 | Unger et al. ............................ 424/450 |

FOREIGN PATENT DOCUMENTS

| | | |
|---|---|---|
| 2 046 094 | 11/1980 | European Pat. Off. . |
| 0 577 215 | 1/1994 | European Pat. Off. . |
| 0 463 228 | 1/1998 | European Pat. Off. . |

OTHER PUBLICATIONS

*The Merck Index*, 10th Edition, pp. 920 (Merck & Co., Rahway, NJ, 1983).

*American Family Physician*, Mar. 1997.

Marsala et al., "Treatment of Acute Pain of Ureteral and Biliary Colic with Naproxen Sodium Administered by the Parenteral Route," *Int. J. Clin. Pharmacol. Res.*, 6:495–500 (1986) (IM an IV injections of naproxen).

L. Kvarnes, "Naproxen Sodium Versus Pentazocine in Treating Postoperative Pain," *Curr. Ther. Res., Clin. Exp.*, 46:259–268 (1989) (IM injections of naproxen).

*The Merck Index*, 10th Edition, pp. 1106 (Merck & Co., Rahway, NJ, 1983).

*Primary Examiner*—Carlos A. Azpuru
*Attorney, Agent, or Firm*—Foley & Lardner

[57] ABSTRACT

Described are an injectable formulation of nanoparticulate naproxen that produces minimal or no pain or burning sensation upon administration, and methods of making and using such a formulation. The injectable formulation comprises nanoparticulate naproxen having a povidone polymer adsorbed on the surface thereof in an amount sufficient to maintain an effective average particle size of less than about 600 nm.

20 Claims, No Drawings

INJECTABLE FORMULATIONS OF NANOPARTICULATE NAPROXEN

BACKGROUND OF THE INVENTION

1. Field of the Invention

The present invention is directed to an injectable formulation of nanoparticulate naproxen that produces minimal or no intramuscular pain or burning sensation upon administration, methods of making such a formulation, and methods of using such a formulation.

2. Description of the Related Art

Naproxen, also known as 6-methoxy-α-methyl-2-napthalene-acetic acid and d-2(6-methoxy-2-naphthyl) propionic acid, is a well-known anti-inflammatory, analgesic, and antipyretic agent. It has been approved in many countries around the world for almost two decades and has a very safe risk-benefit profile. It is sold under the trade names ALEVE®, ANAPROX®, NAPROSYN®, and SYN-FLEX® (all available from Syntex Chemicals, Inc.). See The Merck Index, 10$^{th}$ Edition, pp. 6274 (Merck & Co., Rahway, N.J., 1983).

Naproxen, which is highly water insoluble, i.e., less than 10 mg/ml, has the following chemical structure:

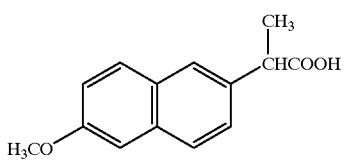

Naproxen is a non-steroidal anti-inflammatory drug (NSAID) often used to relieve the inflammation, swelling, stiffness, and joint pain associated with rheumatoid arthritis, osteoarthritis (the most common form of arthritis), juvenile arthritis, ankylosing spondylitis (spinal arthritis), tendinitis, bursitis, and acute gout. In addition, it is used to treat pain associated with menstrual periods, migraine headaches, and other types of mild to moderate pain.

Naproxen acts by suppressing the production of prostaglandins, which are hormone-like substances that act on local tissues to produce pain and inflammation. Its pharmaceutical forms of delivery include tablets, capsules, and liquids. Delivery characteristics and forms are disclosed in, for example, U.S. Pat. Nos. 3,904,682; 4,009,197; 4,780,320; 4,888,178; 4,919,939; 4,940,588; 4,952,402; 5,200,193; 5,354,556; 5,462,747; and 5,480,650, all of which are specifically incorporated by reference. The synthesis of naproxen is described in U.S. Pat. Nos. 3,904,682 and 4,009,197.

Naproxen is a more potent pain reliever than aspirin, especially for menstrual cramps, toothaches, minor arthritis, and injuries accompanied by inflammation, such as tendinitis. The naproxen sodium salt is specifically indicated in the treatment of various types of acute and very high intensity pain because it induces a rapid and sustained remission. In addition, it is possible to obtain a good analgesic effect with few administrations, due to naproxen's particular pharmacokinetics. Tablet formulations of naproxen were approved for OTC ("over the counter" as compared to prescription) marketing by the U.S. Food and Drug Administration in 1994.

Because of naproxen's low solubility, it is generally formulated for oral administration. However, oral administration of naproxen frequently results in gastrointestinal irritation. All NSAIDs produce gastrointestinal symptoms to some degree upon oral administration. Such symptoms most commonly are constipation, gastric burns, diarrhea, stomatitis, dyspepsia, nausea, vomiting, upper abdominal pain, and heartburn. Oral administration may also lead to an ulcer or bleeding from the stomach or duodenum.

Gastrointestinal irritation resulting from oral administration of an NSAID can be significant. Numerous literature articles detail the severity of gastric irritation caused by NSAID compositions. For example, one report states that between 10,000 and 20,000 people in Canada each year are hospitalized with major gastro-intestinal bleeding caused by oral ingestion of NSAIDs, with effects resulting in death for at least 1,000 of these patients. See *Marketplace*, Oct. 24, 1996. Yet another reference states that gastrointestinal complications of NSAID use may be responsible for over 10,000 deaths each year. See *American Family Physician*, March 1997.

Injectable formulations of naproxen are preferable over oral administration forms for several reasons. First, such formulations can lessen or eliminate side effects of gastrointestinal irritation. Second, intravenous (IV) or intramuscular (IM) administration of a drug results in a significantly shorter response time as compared to oral administration. Moreover, injectable formulations of pain medication are also preferable for post-operative health care, where oral administration may not be feasible. Injectable formulations of naproxen are particularly preferred, as naproxen is not addictive, in contrast to other injectable formulations of drugs, such as morphine and ketorolac (Toradol®).

Injectable formulations of naproxen have been used prior to the present invention. See Marsala et al., "Treatment of Acute Pain of Ureteral and Biliary Colic with Naproxen Sodium Administered by the Parenteral Route," *Int. J. Clin. Pharmacol. Res.*, 6:495–500 (1986) (IM and IV injections of naproxen); L. Kvarnes, "Naproxen Sodium Versus Pentazocine in Treating Postoperative Pain," *Curr. Ther. Res., Clin. Exp.*, 46:259–268 (1989) (IM injections of naproxen). However, injectable naproxen formulations are difficult to formulate due to the low solubility of naproxen. Moreover, current injectable formulations of naproxen are undesirable because they produce intense pain and/or a burning sensation upon administration. Such pain is counter-productive, particularly as the patient to be treated is generally already suffering from intense pain. Thus, the pain upon administration interferes with patient treatment, and has led to the use of alternative, but less desirable, injectable pain medications.

There is currently a need for a safe and effective injectable formulation of naproxen that produces minimal or no pain or burning sensation upon administration. In addition, there is a need in the art for methods of making and methods of using such naproxen formulations. The present invention satisfies these needs.

SUMMARY OF THE INVENTION

The present invention is directed to the surprising and unexpected discovery of a new injectable formulation of naproxen that produces minimal or no pain or burning sensation upon administration. The injectable formulation comprises nanoparticulate naproxen having a povidone polymer adsorbed on the surface thereof in an amount sufficient to maintain an effective average particle size of less than about 600 nm. Preferably, the effective average particle size of the nanoparticulate naproxen is less than about 450 nm, more preferably less than about 300 nm, even more preferably less than about 250 nm, and most preferably less than about 100 nm. Nanoparticulate compositions were first described in U.S. Pat. No. 5,145,684 ("the '684 patent"), which is specifically incorporated herein by reference.

The invention provides for compositions comprising high naproxen concentrations in low injection volumes, with rapid drug dissolution upon administration.

In another aspect of the invention there is provided a method of preparing injectable nanoparticulate naproxen formulations. The method comprises: (1) dispersing naproxen in a liquid dispersion medium comprising a povidone polymer with a molecular weight of less than about 40,000 daltons; and (2) mechanically reducing the particle size of the naproxen to an effective average particle size of less than about 600 nm. Preferably, the pH of the liquid dispersion medium is maintained within the range of from about 3 to about 8 during the size reduction process.

Yet another aspect of the present invention provides a method of treating a mammal requiring anti-inflammatory, analgesic, or antipyretic treatment comprising administering to the mammal the above-described injectable nanoparticulate naproxen formulation.

It is to be understood that both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE INVENTION

The present invention is directed to the surprising and unexpected discovery of a new injectable formulation of naproxen that produces minimal or no pain or burning sensation upon administration. The injectable composition comprises nanoparticulate naproxen having a povidone polymer with a molecular weight of less than about 40,000 daltons adsorbed on the surface thereof in an amount sufficient to maintain an effective average particle size of less than about 600 nm. Preferably, the effective average particle size of the nanoparticulate naproxen is less than about 450 nm, more preferably less than about 300 nm, even more preferably less than about 250 nm, and most preferably less than about 100 nm.

Naproxen has a pKa of 4.4. Below its pKa of 4.4, the solubility of naproxen is about 20 micrograms/ml. However, above a pKa of 4.4, the solubility of naproxen is about 3 mg/ml. It is preferred that the nanoparticulate naproxen/povidone polymer pharmaceutical formulation of the invention has a pH of between about 6 to about 7.

In human therapy, it is important to provide a naproxen dosage form that delivers the required therapeutic amount of the drug in vivo, and that renders the drug bioavailable in a rapid and constant manner. The injectable nanoparticulate naproxen formulations of the present invention satisfies these needs.

Povidone Polymers

Povidone polymers, also known as polyvidon(e), povidonum, PVP, and polyvinylpyrrolidone, are sold under the trade names Kollidon® (BASF Corp.) and Plasdone® (ISP Technologies, Inc.). They are polydisperse macromolecular molecules, with a chemical name of 1-ethenyl-2-pyrrolidinone polymers and 1-vinyl-2-pyrrolidinone polymers. Povidone polymers are produced commercially as a series of products having mean molecular weights ranging from about 10,000 to about 700,000 daltons. To be useful as a surface modifier for a drug compound to be administered to a mammal, the povidone polymer must have a molecular weight of less than about 40,000 daltons, as a molecular weight of greater than 40,000 daltons would have difficulty clearing the body.

Povidone polymers are prepared by, for example, Reppe's process, comprising: (1) obtaining 1,4-butanediol from acetylene and formaldehyde by the Reppe butadiene synthesis; (2) dehydrogenating the 1,4-butanediol over copper at 200° to form γ-butyrolactone; and (3) reacting γ-butyrolactone with ammonia to yield pyrrolidone. Subsequent treatment with acetylene gives the vinyl pyrrolidone monomer. Polymerization is carried out by heating in the presence of $H_2O$ and $NH_3$. See The Merck Index, $10^{th}$ Edition, pp. 7581 (Merck & Co., Rahway, N.J., 1983).

The manufacturing process for povidone polymers produces polymers containing molecules of unequal chain length, and thus different molecular weights. The molecular weights of the molecules vary about a mean or average for each particular commercially available grade. Because it is difficult to determine the polymer's molecular weight directly, the most widely used method of classifying various molecular weight grades is by K-values, based on viscosity measurements. The K-values of various grades of povidone polymers represent a function of the average molecular weight, and are derived from viscosity measurements and calculated according to Fikentscher's formula.

The weight-average of the molecular weight, Mw, is determined by methods that measure the weights of the individual molecules, such as by light scattering. Table 1 provides molecular weight data for several commercially available povidone polymers, all of which are soluble.

TABLE 1

| Povidone | K-Value | Mv (Daltons)** | Mw (Daltons)** | Mn (Daltons)** |
| --- | --- | --- | --- | --- |
| Plasdone C-15 ® | 17 ± 1 | 7,000 | 10,500 | 3,000 |
| Plasdone C-30 ® | 30.5 ± 1.5 | 38,000 | 62,500* | 16,500 |
| Kollidon 12 PF ® | 11–14 | 3,900 | 2,000–3,000 | 1,300 |
| Kollidon 17 PF ® | 16–18 | 9,300 | 7,000–11,000 | 2,500 |
| Kollidon 25 ® | 24–32 | 25,700 | 28,000–34,000 | 6,000 |

*Because the molecular weight is greater than 40,000 daltons, this povidone polymer is not useful as a surface stabilizer for a drug compound to be administered parenterally (i.e., injected).
**Mv is the viscosity-average molecular weight, Mn is the number-average molecular weight, and Mw is the weight average molecular weight. Mw and Mn were determined by light scattering and ultracentrifugation, and Mv was determined by viscosity measurements.

Based on the data provided in Table 1, exemplary preferred commercially available povidone polymers include, but are not limited to, Plasdone C-15®, Kollidon 12 PF®, Kollidon 17 PF®, and Kollidon 25®.

Injectable Nanoparticulate Naproxen Formulations

The invention provides injectable nanoparticulate naproxen formulations that can comprise high drug concentrations in low injection volumes, with rapid drug dissolution upon administration. Preferred compositions comprise, based on % w/w:

| | |
|---|---|
| naproxen | 5–50% |
| povidone polymer | 0.1–50% |
| preservatives | 0.05–0.25% |
| pH adjusting agent | pH about 6 to about 7 |
| water for injection | q.s. |

Exemplary preservatives include methylparaben (about 0.18% based on % w/w), propylparaben (about 0.02% based on % w/w), phenol (about 0.5% based on % w/w), and benzyl alcohol (up to 2% v/v). An exemplary pH adjusting agent is sodium hydroxide, and an exemplary liquid carrier is sterile water for injection. Other useful preservatives, pH adjusting agents, and liquid carriers are well-known in the art.

Methods of Making Injectable Naproxen Formulations

In another aspect of the invention there is provided a method of preparing the injectable nanoparticulate naproxen formulations of the invention. The method comprises: (1) dispersing naproxen in a liquid dispersion medium comprising a povidone polymer with a molecular weight of less than about 40,000 daltons; and (2) mechanically reducing the particle size of the naproxen to an effective average particle size of less than about 600 nm. Preferably, the effective average particle size of the nanoparticulate naproxen is less than about 450 nm, more preferably less than about 300 nm, even more preferably less than about 250 nm, and most preferably less than about 100 nm. The pH of the liquid dispersion medium is preferably maintained within the range of from about 5.0 to about 7.5 during the size reduction process. Preferably, the dispersion medium used for the size reduction process is aqueous.

Effective methods of providing mechanical force for particle size reduction of naproxen include ball milling, media milling, and homogenization, for example, with a Microfluidizer® (Microfluidics Corp.). Ball milling is a low energy milling process that uses milling media, drug, stabilizer, and liquid. The materials are placed in a milling vessel that is rotated at optimal speed such that the media cascades and reduces the drug particle size by impaction. The media used must have a high density as the energy for the particle reduction is provided by gravity and the mass of the attrition media.

Media milling is a high energy milling process. Drug, stabilizer, and liquid are placed in a reservoir and recirculated in a chamber containing media and a rotating shaft/impeller. The rotating shaft agitates the media which subjects the drug to impaction and sheer forces, thereby reducing the drug particle size.

Homogenization is a technique that does not use milling media. Drug, stabilizer, and liquid (or drug and liquid with the stabilizer added after particle size reduction) constitute a process stream propelled into a process zone, which in the Microfluidizer® is called the Interaction Chamber. The product to be treated is inducted into the pump, and then forced out. The priming valve of the Microfluidizer® purges air out of the pump. Once the pump is filled with product, the priming valve is closed and the product is forced through the interaction chamber. The geometry of the interaction chamber produces powerful forces of sheer, impact, and cavitation which are responsible for particle size reduction. Specifically, inside the interaction chamber, the pressurized product is split into two streams and accelerated to extremely high velocities. The formed jets are then directed toward each other and collide in the interaction zone. The resulting product has very fine and uniform particle or droplet size. The Microfluidizer® also provides a heat exchanger to allow cooling of the product. U.S. Pat. No. 5,510,118, which is specifically incorporated by reference, refers to a process using a Microfluidizer® resulting in sub 400 nm particles.

Using a particle size reduction method, the particle size of naproxen is reduced to an effective average particle size of less than about 600 nm. Preferably, the effective average particle size of the nanoparticulate naproxen is less than about 450 nm, more preferably less than about 300 nm, even more preferably less than about 250 nm, and most preferably less than about 100 nm. The naproxen particles can be reduced in size in the presence of a povidone polymer, or the povidone polymer can be added to the naproxen dispersion following particle size reduction.

Naproxen can be added to a liquid medium in which it is essentially insoluble to form a premix. The concentration of the naproxen in the liquid medium can vary from about 5 to about 60%, and preferably is from about 15 to about 50% (w/v), and more preferably about 20 to about 40%. The povidone polymer can be present in the premix or it can be added to the drug dispersion following particle size reduction. The concentration of the povidone polymer can vary from about 0.1 to about 50%, and preferably is from about 0.5 to about 20%, and more preferably from about 1 to about 10%, by weight.

The premix can be used directly by subjecting it to mechanical means to reduce the average naproxen particle size in the dispersion to less than about 600 nm. It is preferred that the premix be used directly when a ball mill is used for attrition. Alternatively, naproxen and the povidone polymer can be dispersed in the liquid medium using suitable agitation, e.g., a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the naproxen particle size conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the desired reduction in particle size. For media milling, the apparent viscosity of the premix is preferably from about 100 to about 1000 centipoise, and for ball milling the apparent viscosity of the premix is preferably from about 1 up to about 100 centipoise. Such ranges tend to afford an optimal balance between efficient particle size reduction and media erosion.

The attrition time can vary widely and depends primarily upon the particular mechanical means and processing conditions selected. For ball mills, processing times of up to five days or longer may be required. Alternatively, processing times of less than 1 day (residence times of one minute up to several hours) are possible with the use of a high shear media mill.

The naproxen particles must be reduced in size at a temperature which does not significantly degrade naproxen. Processing temperatures of less than about 30 to less than about 40° C. are ordinarily preferred. If desired, the processing equipment can be cooled with conventional cooling equipment. Control of the temperature, e.g., by jacketing or immersion of the milling chamber in ice water, is contemplated. Generally, the method of the invention is conveniently carried out under conditions of ambient temperature and at processing pressures which are safe and effective for the milling process. Ambient processing pressures are typical of ball mills, attritor mills, and vibratory mills.

Grinding Media

The grinding media can comprise particles that are preferably substantially spherical in shape, e.g., beads, consisting essentially of polymeric resin. Alternatively, the grinding media can comprise a core having a coating of a polymeric resin adhered thereon.

In general, suitable polymeric resins are chemically and physically inert, substantially free of metals, solvent, and monomers, and of sufficient hardness and friability to enable them to avoid being chipped or crushed during grinding. Suitable polymeric resins include crosslinked polystyrenes, such as polystyrene crosslinked with divinylbenzene; styrene copolymers; polycarbonates; polyacetals, such as Delrin® (E.I. du Pont de Nemours and Co.); vinyl chloride polymers and copolymers; polyurethanes; polyamides; poly(tetrafluoroethylenes), e.g., Teflon®(E.I. du Pont de Nemours and Co.), and other fluoropolymers; high density polyethylenes; polypropylenes; cellulose ethers and esters such as cellulose acetate; polyhydroxymethacrylate; polyhydroxyethyl acrylate; and silicone-containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). For biodegradable polymers, contamination from the media itself advantageously can metabolize in vivo into biologically acceptable products that can be eliminated from the body.

The grinding media preferably ranges in size from about 0.01 to about 3 mm. For fine grinding, the grinding media is preferably from about 0.02 to about 2 mm, and more preferably from about 0.03 to about 1 mm in size.

The polymeric resin can have a density from about 0.8 to about 3.0 g/cm$^3$.

In a preferred grinding process the particles are made continuously. Such a method comprises continuously introducing naproxen into a milling chamber, contacting the naproxen with grinding media while in the chamber to reduce the naproxen particle size, and continuously removing the nanoparticulate naproxen from the milling chamber.

The grinding media is separated from the milled nanoparticulate naproxen using conventional separation techniques, in a secondary process such as by simple filtration, sieving through a mesh filter or screen, and the like. Other separation techniques such as centrifugation may also be employed.

Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation. By "an effective average particle size of less than about 600 nm" it is meant that at least 90% of the particles, by weight, have a particle size of less than about 600 nm when measured by the above-noted techniques. In preferred embodiments, the effective average particle size is less than about 450 nm, and more preferably less than about 400 nm. The naproxen particles can also have an effective average particle size of less than about 300 nm, less than about 250 nm, and less than about 100 nm. With reference to the effective average particle size, it is preferred that at least 90%, more preferably at least 95%, and most preferably at least 99% of the particles have a particle size less than the effective average particle size. In particularly preferred embodiments essentially all of the particles have a size less than about 600 nm.

While applicants do not wish to be bound by theoretical mechanisms, it is believed that the povidone polymer hinders the flocculation and/or agglomeration of the naproxen particles by functioning as a mechanical or steric barrier between the particles, minimizing the close, interparticle approach necessary for agglomeration and flocculation.

Method of Treatment

Yet another aspect of the present invention provides a method of treating a mammal, including a human, requiring anti-inflammatory, analgesic, or antipyretic treatment comprising administering to the mammal the injectable nanoparticulate naproxen formulation of the invention. Particularly advantageous features of the present invention include that the pharmaceutical formulation of the invention exhibits unexpectedly rapid drug absorption upon administration, and produces minimal or no pain or irritation upon administration. In addition, the injectable formulation of the invention can provide a high naproxen concentration in a small volume to be injected. A general protocol for administration comprises a bolus injection of naproxen, with one continuous fast injection, rather than a slow infusion of the drug.

Sterile Product Manufacturing

Development of injectable compositions requires the production of a sterile product. The manufacturing process of the present invention is similar to typical known manufacturing processes for sterile suspensions. A typical sterile suspension manufacturing process flowchart is as follows:

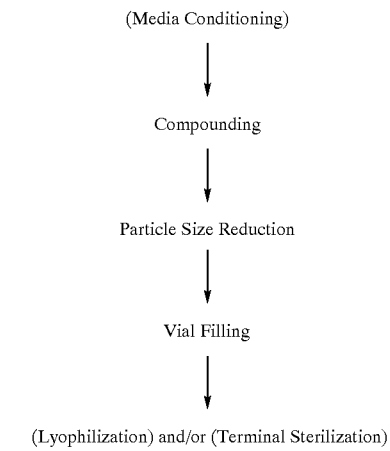

As indicated by the optional steps in parentheses, some of the processing is dependent upon the method of particle size reduction and/or method of sterilization. For example, media conditioning is not required for a milling method that does not use media. If terminal sterilization is not feasible due to chemical and/or physical instability, aseptic processing can be used.

The following examples are given to illustrate the present invention. It should be understood, however, that the invention is not to be limited to the specific conditions or details described in these examples

EXAMPLE 1

The purpose of this example was to evaluate the use of different types of surface modifiers for the preparation of an injectable nanoparticulate formulation of naproxen.

The study was conducted by screening eleven surface stabilizers to identify the most suitable stabilizer for parenteral administration of naproxen. The dispersions were formulated at 40% solids to 2.4% surface stabilizer.

TABLE 2

| Surface Stabilizer | Manufacturer | Results |
|---|---|---|
| Plasdone C15 ® (polyvinyl-pyrrolidone) | ISP Technologies, Inc. | size reduction < 400 nm |
| Kollidon 17PF ® (a polyvinyl-pyrrolidone polymer) | BASF Corp. | size reduction < 400 nm |
| Povidone K30 ® (a polyvinyl-pyrrolidone polymer) | ISP Technologies, Inc. | size reduction < 400 nm |
| Tyloxapol | Nycomed, Inc. | size reduction >400 nm |
| Pluronic F68 ® (a high molecular weight poly-oxyalkylene ether) | BASF Corp. | size reduction >400 nm |
| Pluronic F108 ® (a high molecular weight poly-oxyalkylene ether) | BASF Corp. | size reduction >400 nm |
| Tween 80 ® (a polyoxyethylene sorbitan fatty acid ester) | ICI Americas | size reduction >400 nm |
| dioctylsulfo-succinate (CAS No. 577-11-7; aka Docusate Sodium) | Ashland Chem. Co., Columbus, OH | size reduction >400 nm |
| B20-5000 ® (a triblock copolymer surface modifier) | Dow Chemical | size reduction >400 nm |
| B20-5000-sulfonated (a triblock copolymer surface modifier) | Dow Chemical | size reduction >400 nm |
| lecithin (CAS No. 8002-43-5) | Ashland Chem. Co., Columbus, OH | size reduction >400 nm |
| Povidone K30 ® and Pluronic F108 ® | ISP Technologies, Inc. and BASF Corp. | size reduction >400 nm |

Only the use of the povidone polymers Plasdone C15, Povidone K30®, and Kollidon 17PF® resulted in a nanoparticulate naproxen composition having an effective average particle size of less than about 400 nm.

EXAMPLE 2

The purpose of this example was to determine the rates of absorption for intravenously and intramuscularly administered naproxen.

The plasma concentration of naproxen ($\mu$g/ml) in rabbits after administration of 15 mg/kg by either the IV or IM routes versus time in hours was determined. The method used for quantification of naproxen in rabbit plasma was modified from a procedure by Shimek et al., *Journal of pharm. Sci.*, 15:436–439 (1982).

For IM administration, the mean peak plasma level concentration ($C_{max}$) of 45±9 $\mu$g/ml was reached at two hours. The absorption after IM injection was rapid with a mean plasma concentration of 23.5±5.1 $\mu$g/ml at 30 minutes after injection. At twelve hours post injection, plasma concentrations were still measurable at 5.2±3.4 $\mu$g/ml.

Pharmacokinetic Analysis: The area-under-curve value (AUC) (i.e., plasma -concentration time curve) calculations for the IM and IV routes were 287.1 $\mu$g/ml·hr and 212.0 $\mu$g/ml·hr, respectively. Mean clearance was calculated to be 3.4 ml/min after IM administration and 5.1 ml/min following IV administration. The calculated $T_{1/2}$ (the time period in which the maximum plasma concentration drops by half) following IM administration was 6.9 hours, and 7.0 hours following IV administration.

EXAMPLE 3

The purpose of this example was to demonstrate the feasibility of using a Microfluidizer® for aseptically producing an injectable formulation of a naproxen colloidal dispersion.

A Microfluidizer®, Model No. M110EH (Microfluidics Corp.), was successfully used to produce a sterile colloidal dispersion of naproxen suitable for injection. The naproxen slurry was heat sterilized prior to microfluidizing.

EXAMPLE 4

The purpose of this example was to determine the potential local irritation of an injectable nanoparticulate naproxen formulation when administered intramuscularly to rats. This information correlates to the irritation or pain experienced upon administration of the formulation.

Test Formulation

Injectable nanoparticulate naproxen having a concentration of 489 mg/ml was used, comprising 489 mg/ml naproxen, 40 mg/ml of ISP Plasdone™ C15, 1.9 mg/ml methylparaben (preservative), and 0.2 mg/ml propylparaben. Dosages of 49 and 134 mg/kg were administered intramuscularly. The intramuscular route was chosen because it is a possible route of administration to human. The test and control articles were stored at room temperature and protected from light.

Test animals

Twenty male Albino rats (Sprague-Dawley Crl:CD®) were used for the study, obtained from Charles River. The animals were laboratory bred and were experimentally naive at the outset of the study. Animals selected for use were as uniform in age and weight as possible. they were approximately 7–8 weeks of age, and their body weights ranged from 210.7 to 247.0 gm. Each animal was identified by a unique number via an ear tag. All animals were acclimated to laboratory conditions for approximately 12 days prior to study initiation, and the animals were housed individually in stainless-steel cages.

PMI Feeds, Inc.®, Certified Rodent Chow was available ad libitum via food hoppers. No contaminants are known to be present in the certified diet that would interfere with the results of the study. Tap water was available ad libitum via automatic watering device or water bottle. The water was routinely analyzed for contaminants. No contaminants are known to be present in the water that would interfere with the results of the study.

All animals were kept in one room and with no additional studies or other species housed in the same room. The room was well ventilated (>10 air changes per hour) with 100% fresh air (no air recirculation). A 12-hour light/12-hour dark photoperiod was maintained. Room temperature and relative humidity were set to be maintained between 22±3° C. and 40 to 70%, respectively.

Administration Protocol and Methods

The twenty test animals were assigned to treatment groups as shown in Table 3 below. Each animal received a single intramuscular injection of the test article and the vehicle in distinct previously shaven sites of contralateral legs: thigh muscle of the right and left hind legs, respectively. Prior to the day of dosing (designated Day 1 of the study), all animals were fasted overnight. Following dosing, animals were returned to their cages and subsequently provided with hoppers containing food. The animals were evaluated for changes in clinical signs and body weight and the injection sites were examined for any local reaction. Ten animals each were sacrificed at approximately 48 and 96 hours after the IM injection and the injection site areas removed and processed for histopathological examination.

TABLE 3

Treatment Groups

| Group | Number of Males | Treatment | Dose (mg/kg) | Dose Vol. (ml/kg) | Day of Sacrifice |
|---|---|---|---|---|---|
| 1 | 5 | Control | 0 | 0.1 | 3 |
|   |   | Nanonaproxen | 49 | 0.1 |   |
| 2 | 5 | Control | 0 | 0.1 | 5 |
|   |   | Nanonaproxen | 49 | 0.1 |   |
| 3 | 5 | Control | 0 | 0.275 | 3 |
|   |   | Nanonaproxen | 134 | 0.275 |   |
| 4 | 5 | Control | 0 | 0.275 | 5 |
|   |   | Nanonaproxen | 134 | 0.275 |   |

Antemortem Procedures

Animals were observed once daily prior to dosing. During the study, each animal was observed once each morning and afternoon for changes in general appearance and behavior. In addition, the injection sites were examined daily thereafter for local reactions. The severity of any injection site observation was graded and if possible measured (length, width, and height). Body weights were measured prior to dosing and at sacrifice.

1. Clinical Observations and Mortality

Twice daily individual clinical observations are presented in Table 4. No animals died and no treatment-related clinical signs were seen in animals given 49 mg/kg of nanoparticulate naproxen by intramuscular injection. At a dose of 134 mg/kg/treatment-related signs such as chromorhinorrhea, pallor, rough coat, and some chromodacryorrhea and brown staining were observed.

TABLE 4

Clinical Observations

| Test Article | Animal No. | Clinical Observations* |
|---|---|---|
| Nanoparticulate Naproxen; 49 mg/kg For 3 day test period | 311M | Days 1–3: normal |
|  | 312M | Days 1–3: normal |
|  | 313M | Days 1–3: normal |
|  | 314M | Days 1–2: normal<br>Day 3: abrasion neck right side; stain red neck right side; scab scapula right |
|  | 315M | Days 1–3: normal |
| Nanoparticulate Naproxen; 49 mg/kg For 5 day test period | 321M | Days 1–5: normal |
|  | 322M | Days 1–5: normal |
|  | 323M | Day 1: normal<br>Day 2: slight bluish color at injection site 2<br>Days 3–5: normal |
|  | 324M | Days 1–4: normal<br>Day 5: dehydrated; scab at injection site on right hind limb |
|  | 325M | Days 1–5: normal |
| Nanoparticulate Naproxen; 134 mg/kg For 3 day test period | 331M | Day 1: normal<br>Days 2–3: infrequent stool<br>Day 3: chromorhinorrhea, pallor |
|  | 332M | Day 1: normal<br>Days 2–3: infrequent stool; chromorhinorrhea; pallor; rough coat<br>Day 3: chromodacryorrhea-both; brown-stained scrotum |
|  | 333M | Day 1: normal<br>Days 2–3: infrequent stool<br>Day 3: chromorhinorrhea; pallor; dehydrated; scab at right injection site |
|  | 334M | Day 1: normal<br>Days 2–3: infrequent stool; chromorhinorrhea; wet coat pelvic region<br>Day 3: pallor; scabs at both injection sites left and right hind limbs |
|  | 335M | Day 1: normal<br>Days 2–3: infrequent stool<br>Day 3: chromodacryorrhea both; chromorhinorrhea; dehydrated; pallor; diarrhea; dark stool |
| Nanoparticulate Naproxen; 134 mg/kg For 5 day test period | 341M | Day 1: normal<br>Days 2–4: chromorhinorrhea<br>Days 2–5: infrequent stool; pallor<br>Day 3: brown-stained forefeet<br>Days 3–5: rough coat |

TABLE 4-continued

Clinical Observations

| Test Article | Animal No. | Clinical Observations* |
|---|---|---|
| | | Day 4: prostrate |
| | | Day 5: dehydrated; scab at injection sites on right hand limb |
| | 342 | Day 1: normal |
| | | Day 2: chromorhinorrhea |
| | | Days 2–3: infrequent stool |
| | | Days 3–5: rough coat; pallor |
| | | Days 4–5: scabhead |
| | | Day 5: scab at injection sites on left hand limb |
| | 343M | Day 1: normal |
| | | Days 2–5: infrequent stool |
| | | Days 3–5: piloerection; rough coat; dehydrated; pallor |
| | 344M | Day 1: normal |
| | | Day 2: loose stool; chromorhinorrhea |
| | | Days 2–3: infrequent stool |
| | | Days 2–4: rough coat |
| | | Day 5: scabs at injection sites bilaterally |
| | 345M | Day 1: normal |
| | | Days 2–5: infrequent stool; chromorhinorrhea; pallor |
| | | Day 3: rough coat; chromodacryorrhea both |
| | | Days 3–5: brown-stained forefeet |
| | | Day 5: dehydrated; scabs at injection sites on hind limbs |

*Findings exclude mechanical artifacts (clipper abrasions).

2. Body Weight

Individual and group mean body weights are presented in Table 5. The Day 3 low-dose group (49 mg/kg) was inadvertently not fasted for necropsy and, therefore, showed a much larger weight gain than the fasted low-dose group sacrificed on Day 5. However, animals in the high-dose group (134 mg/kg) sacrificed on Days 3 (also, inadvertently not fasted) or 5 showed an overall average weight loss that was considered to be treatment related.

TABLE 5

Individual and Group Mean Body Weights (g)

| Treatment | Animal No. | Day 1 | Day 3* | Day 5 |
|---|---|---|---|---|
| Nanoparticulate Naproxen; 49 mg/kg | 311M | 210.7 | 251.5 | |
| | 312M | 219.4 | 256.6 | |
| | 313M | 224.5 | 260.9 | |
| | 314M | 234.7 | 271.8 | |
| | 315M | 237.3 | 273.0 | |
| | mean | 225.3 | 262.8 | |
| | ±SD | ±11.0 | ±9.4 | |
| Nanoparticulate Naproxen; 49 mg/kg | 321M | 218.9 | | 233.5 |
| | 322M | 216.8 | | 222.4 |
| | 323M | 223.4 | | 229.5 |
| | 324M | 234.6 | | 249.1 |
| | 325M | 241.9 | | 259.3 |
| | mean | 227.1 | | 238.8 |
| | ±SD | ±10.8 | | ±15.1 |
| Nanoparticulate Naproxen; 134 mg/kg | 331M | 215.2 | 203.2 | |
| | 332M | 216.6 | 210.1 | |
| | 333M | 226.7 | 211.0 | |
| | 334M | 228.0 | 216.3 | |
| | 335M | 247.0 | 227.3 | |
| | mean | 226.7 | 213.6 | |
| | ±SD | ±12.7 | ±9.0 | |
| Nanoparticulate Naproxen; 134 mg/kg | 341M | 216.1 | | 192.1 |
| | 342M | 213.0 | | 184.5 |
| | 343M | 226.3 | | 189.7 |
| | 344M | 228.3 | | 208.5 |
| | 345M | 241.5 | | 209.2 |
| | mean | 225.0 | | 196.8 |
| | ±SD | ±11.3 | | ±11.3 |

*Terminal body weight from unfasted animals.

3. Injection Site Evaluation

Individual and group mean dermal irritation (erythema/eschar) and (edema) are presented in Tables 6 and 7, respectively. No erythema/eschar or edema responses were noted in any of the animals (indicated by "0" in Tables 6 and 7).

TABLE 6

Individual and Group Mean Dermal Irritation (Erythema or Eschar) Scores

| Treatment | Animal No. | Day 2 | Day 3 | Day 4 | Day 5 |
|---|---|---|---|---|---|
| Control | 311M | 0 | 0 | | |
| | 312M | 0 | 0 | | |
| | 313M | 0 | 0 | | |
| | 314M | 0 | 0 | | |
| | 315M | 0 | 0 | | |
| | mean | 0 | 0 | | |
| | ±SD | ±0 | ±0 | | |
| Nanoparticulate Naproxen; 49 mg/kg | 311M | 0 | 0 | | |
| | 312M | 0 | 0 | | |
| | 313M | 0 | 0 | | |
| | 314M | 0 | 0 | | |
| | 315M | 0 | 0 | | |
| | mean | 0 | 0 | | |
| | ±SD | ±0 | ±0 | | |
| control | 321M | 0 | 0 | 0 | 0 |
| | 322M | 0 | 0 | 0 | 0 |
| | 323M | 0 | 0 | 0 | 0 |

TABLE 6-continued

Individual and Group Mean Dermal Irritation (Erythema or Eschar) Scores

| Treatment | Animal No. | Day 2 | Day 3 | Day 4 | Day 5 |
|---|---|---|---|---|---|
| | 324M | 0 | 0 | 0 | 0 |
| | 325M | 0 | 0 | 0 | 0 |
| | mean | 0 | 0 | 0 | 0 |
| | ±SD | ±0 | ±0 | ±0 | ±0 |
| Nanoparticulate Naproxen; 49 mg/kg | 321M | 0 | 0 | 0 | 0 |
| | 322M | 0 | 0 | 0 | 0 |
| | 323M | 0 | 0 | 0 | 0 |
| | 324M | 0 | 0 | 0 | 0 |
| | 325M | 0 | 0 | 0 | 0 |
| | mean | 0 | 0 | 0 | 0 |
| | ±SD | ±0 | ±0 | ±0 | ±0 |
| Control | 331M | 0 | 0 | | |
| | 332M | 0 | 0 | | |
| | 333M | 0 | 0 | | |
| | 334M | 0 | 0 | | |
| | 335M | 0 | 0 | | |
| | mean | 0 | 0 | | |
| | ±SD | ±0 | ±0 | | |
| Nanoparticulate Naproxen; 134 mg/kg | 331M | 0 | 0 | | |
| | 332M | 0 | 0 | | |
| | 333M | 0 | 0 | | |
| | 334M | 0 | 0 | | |
| | 335M | 0 | 0 | | |
| | mean | 0 | 0 | | |
| | ±SD | ±0 | ±0 | | |
| control | 341M | 0 | 0 | 0 | 0 |
| | 342M | 0 | 0 | 0 | 0 |
| | 343M | 0 | 0 | 0 | 0 |
| | 344M | 0 | 0 | 0 | 0 |
| | 345M | 0 | 0 | 0 | 0 |
| | mean | 0 | 0 | 0 | 0 |
| | ±SD | ±0 | ±0 | ±0 | ±0 |
| Nanoparticulate Naproxen; 134 mg/kg | 341M | 0 | 0 | 0 | 0 |
| | 342M | 0 | 0 | 0 | 0 |
| | 343M | 0 | 0 | 0 | 0 |
| | 344M | 0 | 0 | 0 | 0 |
| | 345M | 0 | 0 | 0 | 0 |
| | mean | 0 | 0 | 0 | 0 |
| | ±SD | ±0 | ±0 | ±0 | ±0 |

TABLE 7

Individual and Group Mean Dermal Irritation (Edema) Scores

| Treatment | Animal No. | Day 2 | Day 3 | Day 4 | Day 5 |
|---|---|---|---|---|---|
| Control | 311M | 0 | 0 | | |
| | 312M | 0 | 0 | | |
| | 313M | 0 | 0 | | |
| | 314M | 0 | 0 | | |
| | 315M | 0 | 0 | | |
| | mean | 0 | 0 | | |
| | ±SD | ±0 | ±0 | | |
| Nanoparticulate Naproxen; 49 mg/kg | 311M | 0 | 0 | | |
| | 312M | 0 | 0 | | |
| | 313M | 0 | 0 | | |
| | 314M | 0 | 0 | | |
| | 315M | 0 | 0 | | |
| | mean | 0 | 0 | | |
| | ±SD | ±0 | ±0 | | |
| Control | 321M | 0 | 0 | 0 | 0 |
| | 322M | 0 | 0 | 0 | 0 |
| | 323M | 0 | 0 | 0 | 0 |
| | 324M | 0 | 0 | 0 | 0 |
| | 325M | 0 | 0 | 0 | 0 |
| | mean | 0 | 0 | 0 | 0 |
| | ±SD | ±0 | ±0 | ±0 | |
| Nanoparticulate Naproxen; 49 mg/kg | 321M | 0 | 0 | 0 | 0 |
| | 322M | 0 | 0 | 0 | 0 |
| | 323M | 0 | 0 | 0 | 0 |
| | 324M | 0 | 0 | 0 | 0 |
| | 325M | 0 | 0 | 0 | 0 |
| | mean | 0 | 0 | 0 | 0 |
| | ±SD | ±0 | ±0 | ±0 | ±0 |
| control | 331M | 0 | 0 | | |
| | 332M | 0 | 0 | | |
| | 333M | 0 | 0 | | |
| | 334M | 0 | 0 | | |
| | 335M | 0 | 0 | | |
| | mean | 0 | 0 | | |
| | ±SD | ±0 | ±0 | | |
| Nanoparticulate Naproxen; 134 mg/kg | 331M | 0 | 0 | | |
| | 332M | 0 | 0 | | |
| | 333M | 0 | 0 | | |
| | 334M | 0 | 0 | | |
| | 335M | 0 | 0 | | |
| | mean | 0 | 0 | | |
| | ±SD | ±0 | ±0 | | |
| control | 341M | 0 | 0 | 0 | 0 |
| | 342M | 0 | 0 | 0 | 0 |
| | 343M | 0 | 0 | 0 | 0 |
| | 344M | 0 | 0 | 0 | 0 |
| | 345M | 0 | 0 | 0 | 0 |
| | mean | 0 | 0 | 0 | 0 |
| | ±SD | ±0 | ±0 | ±0 | ±0 |
| Nanoparticulate Naproxen; 134 mg/kg | 341M | 0 | 0 | 0 | 0 |
| | 342M | 0 | 0 | 0 | 0 |
| | 343M | 0 | 0 | 0 | 0 |
| | 344M | 0 | 0 | 0 | 0 |
| | 345M | 0 | 0 | 0 | 0 |
| | mean | 0 | 0 | 0 | 0 |
| | ±SD | ±0 | ±0 | ±0 | ±0 |

Postmortem Procedures

All animals were terminated by $CO_2$ asphyxiation and exsanguination. Gross necropsy was limited to examination of the injection sites. No treatment-related effects were observed as all injection sites (muscle) were normal. One animal (#333) had a single red subcutaneous focus above the muscle injection site that probably corresponded to hemorrhage. Injection site scabs noted on the twice daily clinical observations generally corresponded to dried blood. Although no internal gross examination was performed, two high-dose animals (#'s 332 and 333) were observed to have severely distended stomachs filled with fluid and gas when they were terminated by exsanguination. These observed findings were considered to be treatment related.

Conclusion

No dermal irritation was observed following single-dose intramuscular administration of injectable nanoparticulate naproxen at doses of 49 mg/kg and 134 mg/kg, in comparison to the control animals. Similarly, no treatment-related clinical signs were observed at doses of 49 mg/kg. At a dose of 134 mg/kg, the following clinical signs were observed: chromorhinorrhea, pallor, rough coat, some chromodacryorrhea, and brown staining.

At necropsy, no treatment-related gross findings at the injection sites were observed. Similarly, histopathological examination of the injection sites revealed no treatment-related effects.

It will be apparent to those skilled in the art that various modifications and variations can be made in the compositions, methods, and uses of the present invention without departing from the spirit or scope of the invention. Thus, it is intended that the present invention cover the modifications and variations of this invention provided they come within the scope of the appended claims and their equivalents.

We claim:

1. A nanoparticulate injectable pharmaceutical composition comprising: (1) naproxen particles having an effective average particle size of less than about 600 nm; (2) a povidone polymer adsorbed on the surface of the naproxen particles, wherein the povidone polymer has a molecular weight of about 40,000 daltons or less; and (3) a pharmaceutically acceptable carrier.

2. The composition of claim 1, wherein the effective average particle size of the naproxen particles is less than about 450 nm.

3. The composition of claim 1, wherein the effective average particle size of the naproxen particles is selected from the group consisting of less than about 400 nm, less than about 300 nm, less than about 250 nm, and less than about 100 nm.

4. The composition of claim 1, wherein the povidone polymer is present in an amount of about 0.1 to about 50% (w/w) based on the total weight of the naproxen and povidone polymer.

5. The composition of claim 1, wherein the naproxen is present in an amount of about 5.0 to about 50% (w/w), by weight.

6. A method of treating a mammal comprising administering to the mammal an effective amount of a nanoparticulate injectable pharmaceutical composition comprising: (1) naproxen particles having an effective average particle size of less than about 600 nm; (2) a povidone polymer adsorbed on the surface of the naproxen particles, wherein the povidone polymer has a molecular weight of about 40,000 daltons or less; and (3) a pharmaceutically acceptable carrier.

7. The method of claim 6, wherein the effective average particle size of the naproxen particles is less than about 450 nm.

8. The method of claim 7, wherein the effective average particle size of the naproxen particles is selected from the group consisting of less than about 400 nm, less than about 300 nm, less than about 250 nm, and less than about 100 nm.

9. The method of claim 6, wherein the povidone polymer has a molecular weight of about 40,000 daltons.

10. The method of claim 6, wherein the povidone polymer has a molecular weight of less than about 40,000 daltons.

11. A method of preparing a nanoparticulate injectable pharmaceutical composition that produces minimal or no pain or irritation upon administration, wherein the composition comprises: (1) naproxen particles having an effective average particle size of less than about 600 nm; (2) a povidone polymer adsorbed on the surface of the naproxen particles, wherein the povidone polymer has a molecular weight of about 40,000 daltons or less; and (3) a pharmaceutically acceptable carrier, wherein the method comprises:

(a) dispersing the naproxen particles in a liquid dispersion medium comprising a povidone polymer; and (b) mechanically reducing the particle size of the naproxen to an effective average particle size of less than about 600 nm.

12. The method of claim 11, wherein the effective average particle size of the naproxen particles is less than about 450 nm.

13. The method of claim 12, wherein the effective average particle size of the naproxen particles is selected from the group consisting of less than about 400 nm, less than about 300 nm, less than about 250 nm, and less than about 100 nm.

14. A method of preparing a nanoparticulate injectable pharmaceutical composition comprising: (1) naproxen particles having an effective average particle size of less than about 600 nm; (2) a povidone polymer adsorbed on the surface of the naproxen particles, wherein the povidone polymer has a molecular weight of about 40,000 daltons or less; and (3) a pharmaceutically acceptable carrier, wherein the method comprises:

(a) dispersing the naproxen particles in a liquid dispersion;

(b) mechanically reducing the particle size of the naproxen to an effective average particle size of less than about 600 nm; and (c) adding a povidone polymer to the dispersion of naproxen particles.

15. The method of claim 14, wherein the effective average particle size of the naproxen particles is less than about 450 nm.

16. The method of claim 15, wherein the effective average particle size of the naproxen particles is selected from the group consisting of less than about 400 nm, less than about 300 nm, less than about 250 nm, and less than about 100 nm.

17. The composition of claim 1, wherein the pH of the nanoparticulate composition is between about 6 to about 7.

18. The method of claim 6, wherein the pH of the nanoparticulate composition is between about 6 to about 7.

19. The method of claim 11, wherein the pH of the nanoparticulate composition is between about 6 to about 7.

20. The method of claim 14, wherein the pH of the nanoparticulate composition is between about 6 to about 7.

* * * * *